United States Patent [19]

Chew et al.

[11] Patent Number: 4,855,491

[45] Date of Patent: Aug. 8, 1989

[54] METHOD FOR SELECTIVELY REMOVING PROCESS STREAM IMPURITIES UTILIZING REVERSE OSMOSIS

[75] Inventors: Calvin T. Chew, Warrenville; John C. Gee, Aurora, both of Ill.

[73] Assignee: Amoco Corporation, Chicago, Ill.

[21] Appl. No.: 185,421

[22] Filed: Apr. 25, 1988

[51] Int. Cl.$^4$ .................................. C07C 51/265
[52] U.S. Cl. .................................. 562/414; 562/409; 562/412; 562/413; 562/416; 210/500.3
[58] Field of Search ............... 562/409, 412, 413, 414, 562/416; 210/500.3

[56] References Cited

U.S. PATENT DOCUMENTS 3,092,658  6/1963  Baldwin et al. .................... 562/413
3,170,768  2/1965  Baldwin ............................. 422/189

Primary Examiner—Donald B. Moyer
Assistant Examiner—Julie K. Parker

Attorney, Agent, or Firm—Gunar J. Blumberg; William M. Magidson; Ralph C. Medhurst

[57] ABSTRACT

A method for the continuous, catalytic production of an aromatic carboxylic acid product by liquid-phase, exothermic oxidaion of an aromatic alkyl with an oxygen-containing gas and a solvent medium in an oxidation reactor and utilizing reverse osmosis is disclosed. In particular, a multiple ingredient or component-containing slurry product stream is withdrawn from the reactor, the slurry product stream is then separated to produce a product-containing stream and at least one mother liquor stream which contains, in addition to a number of desirable process stream components, such as oxidation reaction catalysts, a number of undesirable process stream impurities. The impurities are selectively removed from the mother liquor stream by passing at least a portion of the mother liquor stream through a reverse osmosis separation device to produce a catalyst-bearing stream having a relatively lesser impurities-to-catalyst weight ratio and a purge stream having a relatively greater impurities-to-catalyst weight ratio.

8 Claims, 2 Drawing Sheets

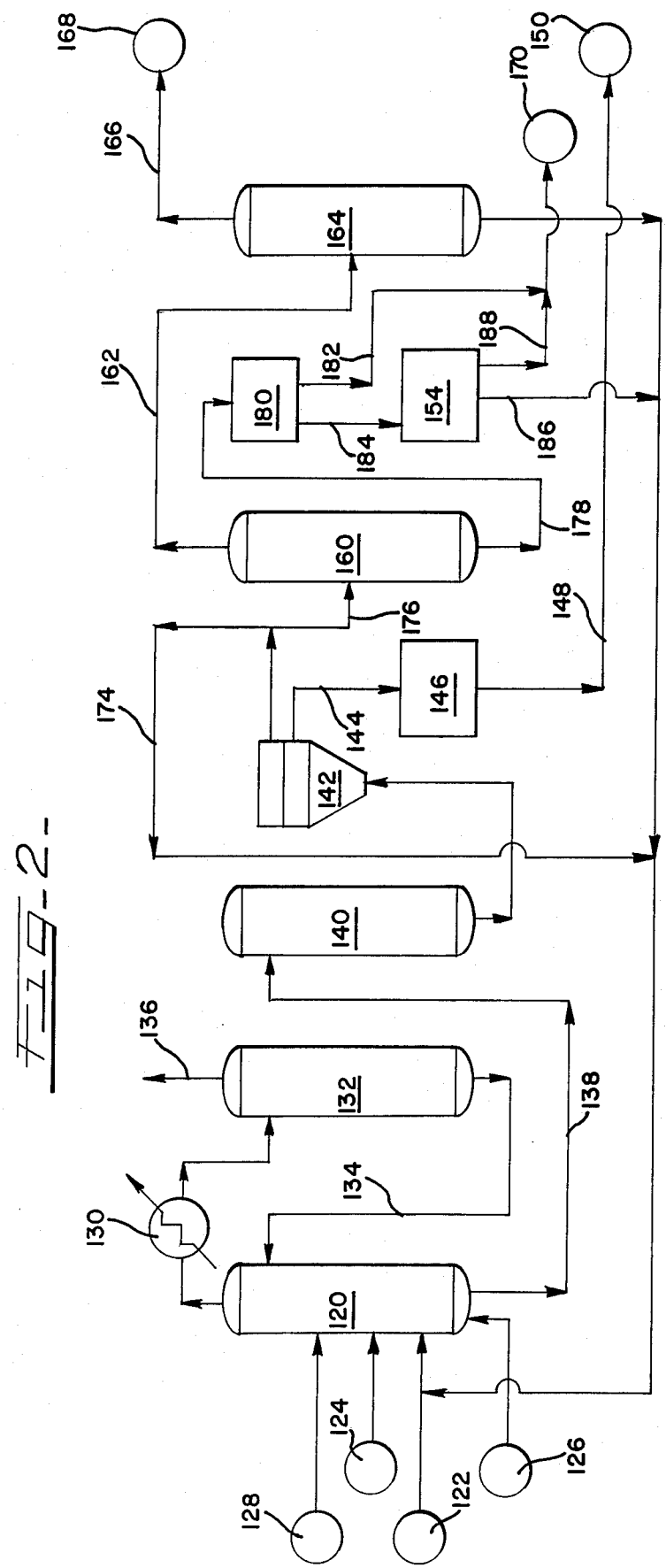

METHOD FOR SELECTIVELY REMOVING PROCESS STREAM IMPURITIES UTILIZING REVERSE OSMOSIS

TECHNICAL FIELD

The present invention relates to a method for selectively removing process stream impurities by reverse osmosis. More particularly, the present invention is directed to a method for selectively removing certain impurities from certain multiple component-containing aromatic carboxylic acid-bearing plant streams by reverse osmosis separation.

BACKGROUND OF THE INVENTION

Aromatic alkyls are commonly catalytically oxidized, in the liquid phase and within pressurized oxidation reactors, to produce aromatic carboxylic acids. U.S. Pat. Nos. 3,092,658 and 3,170,768, both to Baldwin, are illustrative. Typically, a reaction medium within the reactor includes the aromatic alkyl, the oxidation catalyst, an oxygen-containing gas, and a solvent. The oxidation reaction is exothermic, the solvent is volatilizable and, by means of a reflux system, is used to control temperature of the reaction medium. In particular, a substantial portion of the reaction-generated heat is removed by evaporating a portion of the solvent from the reactor and withdrawing the thus-evaporated portion from the reactor as a reactor overhead vapor stream. The vapor stream is then partially condensed, and the condensate is returned to the reactor.

A product stream from the reactor contains, in addition to the produced aromatic carboxylic acid, minor amounts of catalyst, solvent, oxidation reaction by-products, and certain other process stream impurities. One process stream impurity that is present is sodium ion. The presence of sodium ions is undesirable; however, they enter process streams when certain sodium-containing compounds such as sodium hydroxide are utilized to unplug certain transfer lines or to clean the process equipment.

The reactor product stream is passed through separation equipment for producing a concentrated aromatic carboxylic acid product stream and a residue stream which contains a major portion of the catalyst, the solvent, the oxidation-reaction by-products, and the process stream impurities that had been contained in the reactor product stream. Inasmuch as the catalyst contained in such a residue stream still possesses useful catalytic activity, it is desirable to recover and return at least a portion of the residue stream-contained catalyst to the oxidation reactor. To that end, the residue stream currently is separated into a catalyst-depleted stream and one or more catalyst-containing return streams that are returned to the reactor. The return streams, at present, also contain the oxidation reaction by-products as well as the other process stream impurities mentioned above. Over a period of time, the impurity concentration in the oxidation reactor builds to a point where the impurity concentration can enhance formation rates of undesirable reaction by-products.

Conventional methods of purging the impurities from the oxidation reactor tend to cause sizable amounts of the oxidation catalyst and solvent to be purged as well. Current catalyst and solvent costs make such an impurities-purging method to be economically undesirable. Such a purging method also undesirably reduces product yields.

Substantial efforts have been heretofore expended toward improving separation of the impurities from the above-mentioned catalyst-containing return stream before such stream is returned to the reactor. However, all such known methods to effectively separate the impurities from the catalyst-containing stream prior to its return to the reactor have turned out to be, upon investigation, either technologically impractical, economically undesirable, or both.

Because of the large amounts of the various aromatic carboxylic acid products that are currently being produced, it is desirable to provide a cost-effective and technologically-feasible method to effectively separate the impurities from the catalyst-containing stream prior to its return to the reactor. The present invention provides a substantial advance toward that objective.

SUMMARY OF THE INVENTION

The present invention provides a process that utilizes reverse osmosis in a practical separation technique for selectively removing a number of undesired constituents from a multiple component process stream without adversely effecting the yield of the desired end product.

The present invention contemplates a method for the continuous, catalytic production of an aromatic carboxylic acid product by liquid phase, exothermic oxidation of an aromatic alkyl with an oxygen-containing gas and a solvent medium in an oxidation reactor wherein a multiple ingredient or component-containing slurry product stream is withdrawn from the reactor, then separated to produce a product-containing stream and at least one mother liquor stream which is then subjected to reverse osmosis separation to remove a number of undesirable process stream impurities such as sodium ions, polar organic compounds, and the like, therefrom. At least a portion of the mother liquor stream is passed through reverse osmosis separation device and produces a catalyst-bearing stream having a relatively lesser impurities-to-catalyst weight ratio which can be recycled to the reactor and a purge stream having a relatively greater impurities-to-catalyst weight ratio.

BRIEF DESCRIPTION OF THE DRAWINGS

In the drawings,

FIG. 2 is a process flow diagram illustrating another preferred embodiment of the present invention.

Figure 1:
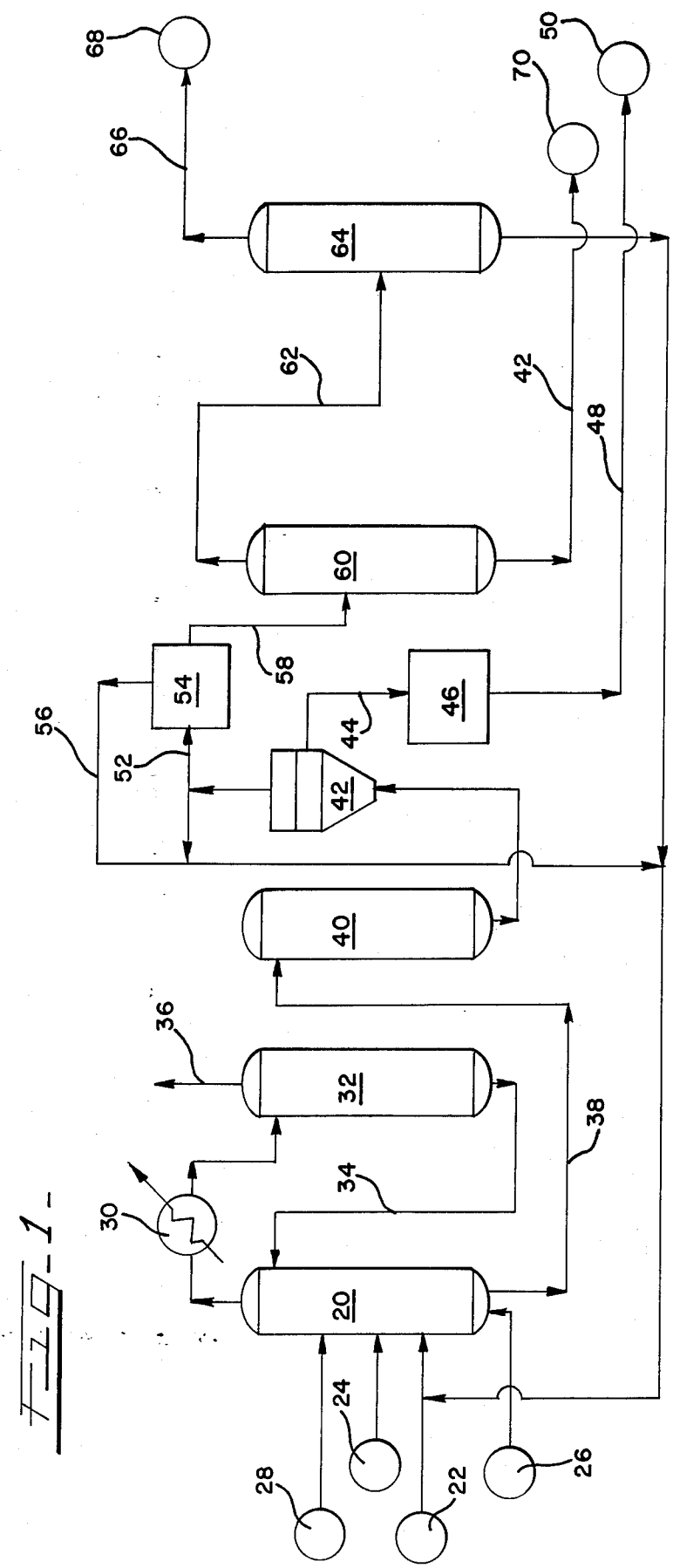
FIG. 1 is a process flow diagram illustrating one preferred embodiment of the present invention.

In the foregoing FIGURES, numerals having the same last two digits identify process elements performing the same or similar functions.

DETAILED DESCRIPTION OF PREFERRED EMBODIMENTS

While the present invention is susceptible to embodiment in various forms, there are shown in the accompanying FIGURES, and hereinafter described in detail, two preferred embodiments of the invention. The present disclosure, however, is to be considered as an exemplification of the present invention without limitation to the specific embodiments illustrated.

Referring to FIG. 1, there is shown an embodiment of a method for selectively removing certain impurities from an aromatic carboxylic acid-containing plant stream while utilizing reverse osmosis separation, all in accordance with the principles of the present invention.

Solvent, an oxygen-containing gas, the aromatic alkyl to be oxidized, and a suitable catalyst are fed continuously into an oxidation reactor 20, maintained at desired temperature and pressure conditions, to produce an aromatic carboxylic acid product. In particular, to produce terephthalic acid (TA), solvent source 22 supplies acetic acid as solvent and aromatic alkyl source 24 supplies para-xylene. The preferred oxygen-containing gas from source 26 is air. The oxygen-containing gas is added to reactor 20 in greater than stoichiometric amounts to minimize formation of undesirable by-products. Catalyst source 28 preferably supplies cobalt and manganese as catalysts for oxidation, and bromine as the renewable source of free radicals. The preferred reactor operating conditions for production of TA, are a temperature of about 175 to about 230 degrees C. and a pressure of about 150 to about 435 psig.

The reaction is exothermic. A portion of the heat of reaction is removed from reactor 20 by condensing vaporized solvent in condenser 30, passing the condensate to gas-liquid separator 32, and refluxing the thus condensed solvent back to reactor 20 via conduit 34. Gases are vented from separator 32 via conduit 36. The aromatic carboxylic acid product along with certain impurities and a number of other ingredients or components are conveyed via conduit 38 to a surge vessel 40. Surge vessel 40 is generally operated at a lower temperature and pressure than reactor 20.

When the solvent is acetic acid and the aromatic carboxylic acid product is TA, the reactor effluent in conduit 38 is a slurry, because TA dissolves only to a limited extent in acetic acid. The multiple ingredient or component-containing slurry product stream from reactor 20 is then passed from surge vessel 40 to centrifuge 42 which, in turn, separates the slurry product stream into a product-containing stream and at least one mother liquor stream. Such a mother liquor stream contains, in addition to a number of desirable process stream components such as oxidation reaction catalyst, a number of undesirable process stream impurities that are subsequently removed in a reverse osmosis device as will be hereinafter described in greater detail.

The product-containing stream is passed via a conduit 44 to product dryer 46. Crystalline aromatic carboxylic acid product is passed from dryer 46 via conduit or transfer line 48 to suitable storage site 50.

A portion of the generated mother liquor stream is passed via conduit 52 to reverse osmosis device 54 which selectively produces a catalyst-bearing and impurities-depleted retentate stream as well as an impurities-containing permeate or effluent stream. The retentate stream has a relatively lower weight ratio of sodium-to-catalyst than the permeate stream. Similarly, the retentate stream has a relatively lower weight ratio of polar aromatic acids-to-catalyst than the permeate stream. The retentate stream is returned via a conduit 56 to reactor 20. The impurities-containing effluent stream or permeate from reverse osmosis device 54 is passed via conduit 58 to residue still 60 which separates water and solvent from the residue. Water and solvent are passed by conduit 62 to a solvent-dehydration tower 64. From tower 64, water is removed via conduit 66 to a suitable site 68 for further processing, re-use or discharge from the system. Residue from still 60, is purged to a suitable storage site 70 via conduit 42.

In the embodiment of the present invention shown in FIG. 2, a portion of the mother liquor from centrifuge 142 is returned to reactor 120 via conduit 174 while the remainder of the mother liquor is passed via conduit 176 to residue still 160. Still 160 separates the water and solvent from the catalyst-containing and impurities-containing mother liquor stream; and the water and solvent are passed via conduit 162 to tower 164 for further separation as described above with reference to the system of FIG. 1. The bottoms from residue still 160 are passed via conduit 178 to catalyst recovery apparatus 180 which separates the catalyst from the residue. The residue is passed via conduit or transfer line 182 to residue-disposal site 170.

From catalyst recovery apparatus 180, the catalyst-containing stream, which also contains a number of undesirable process stream impurities, is passed via conduit 184 to the reverse osmosis device 154 which selectively produces a catalyst-bearing but impurities-depleted retentate stream as well as an impurities-containing permeate or effluent stream or purge stream. The retentate stream has a relatively lesser sodium-to-catalyst weight ratio and the permeate stream has a relatively higher sodium-to-catalyst weight ratio. Likewise, the retentate stream has a relatively lesser polar aromatic acid-to-catalyst weight ratio as compared to the permeate stream. The retentate stream is returned via conduit 186 to reactor 120. The impurities-containing permeate stream from reverse osmosis device 154 is passed via conduit 188 to the residue-disposal site 170.

When the present invention is utilized in connection with a method for continuous, catalytic production of terephthalic acid (TA) by liquid phase, exothermic reaction of para-xylene with air in the presence of acetic acid solvent in an oxidation reactor, a number of features or advantages come to light. First, the selective removal of a substantial portion of the sodium ions as well as certain other impurities such as benzoic, phthalic and/or trimellitic acid that are present in certain process streams significantly decreases the frequency of process upsets due to unanticipated periods of catalyst deactivation. Second, the removal of a substantial portion of the impurities that are present significantly improves product quality as well.

In operation, reverse osmosis device 154 includes a semi-permeable membrane which retains a substantial portion of the specific catalytic ingredients mentioned hereinabove yet passes in the permeate stream a substantial portion of sodium ions present and other impurities present as well as polar aromatic and other organic acids that may be present.

The performance of reverse osmosis device 154 is shown in Table I, below. In this Table and any subsequent Tables, sodium (Na), cobalt (Co), Manganese (Mn) and Bromine (Br) present in the reverse osmosis feed stream are reported in parts per million (by weight) concentrations, as indicated above, while benzoic acid (BA), phthalic acid (OA) and trimellitic acid (TM), present are reported in weight-percent, based on total stream weight. In this and subsequent tables herein, weight-percent of component removed is defined as the ratio of permeate concentration to feed concentration multiplied by a factor of 50.

TABLE I

One Situation Demonstrating
Selective Removal Of Process Stream
Components Utilizing Reverse Osmosis Device

| Aqueous Process Stream Components Supplied to Reverse Osmosis Device | Wt.-% Of Component Removed By | |
|---|---|---|
| | SEPA 89 Membrane | SEPA 50 Membrane |
| Sodium | 10 | 14 |
| Cobalt | 0.2 | 1.7 |
| Manganese | 0.4 | 0.7 |
| Bromine | 1.1 | 2.1 |
| Benzoic Acid | 47 | 43 |
| Phthalic Acid | 17 | 20 |
| Trimellitic Acid | 4.0 | 6.0 |

The data in Table I clearly demonstrate the preferential removal of sodium and polar aromatic acids in the permeate of the reverse osmosis device.

The data in Table II, below, was generated by utilizing a laboratory-simulated process stream, and further illustrates the benefits obtainable by utilizing reverse osmosis for the selective removal of sodium and polar organic acids from the process stream.

TABLE II

Selective Removal Of Simulated Process Stream
Components Utilizing Reverse Osmosis Device

| Aqueous Process Stream Components Supplied to Reverse Osmosis Device | Concentration of | Wt.-% Of Component Removed By | |
|---|---|---|---|
| | | SEPA 89 Membrane | SEPA 92 Membrane |
| Na | 463 | 27 | 38 |
| Co | 465 | 3.1 | 7.5 |
| Mn | 598 | 2.6 | 8.0 |
| Br | 863 | 15 | 24.6 |
| BA | .5 | 37 | 46 |
| OA | .119 | 9 | 20 |
| TM | .145 | 2.1 | 4.1 |

In yet another experiment, a reverse osmosis test cell was equipped with a cellulose acetate membrane (2-inch diameter; SEPA 50 from Osmonics, Inc.) and was fed an aqueous feed composition. The driving force was provided by applying a back pressure of nitrogen to the feed reservoir for the cell. The results are reported in Table III, below.

TABLE III

Separation of Sodium and Benzoic Acid
From Cobalt and Manganese Catalysts

| Feed Composition | wt. (gms) | Comment |
|---|---|---|
| Cobalt acetate tetrahydrate | 1.99 | 0.47 gm Co |
| Manganese acetate tetrahydrate | 2.91 | 0.64 gm Mn |
| 48 wt-% Hydrobromic acid | 1.9 | 0.90 gm Br |
| Sodium acetate trihydrate | 2.96 | |
| Phthalic acid | 1.10 | |
| Trimellitic acid | 1.40 | |
| Benzoic acid | 8.5 | |
| Water | 979 | |
| Operating Conditions | | |
| Feed Rate | 24 cc/hr | |
| Pressure | 220 psi | |
| Temperature | 72° F. | |
| Membrane | Osmonics SEPA 50 (45% NA retention) | |
| Membrane area utilized | 2.1 sq. in. | |
| Results | | |
| Permeate-to-Feed flow rate (ratio) | 20% | |
| Permeate Co Concentration | 66 ppm (wt) | |
| Permeate Mn Concentration | 101 ppm (wt) | |
| Permeate Na Concentration | 227 | |

TABLE III-continued

Separation of Sodium and Benzoic Acid
From Cobalt and Manganese Catalysts

| Permeate benzoic acid Concentration | 0.37 |
|---|---|

In two experiments a reverse osmosis cell was equipped with membranes compatible for use with acetic acid (2-inch diameter; B-15 membrane from DuPont Permasep Products and MR-01 membrane from Osmonics, Inc.) and was fed with an authentic sample of plant process stream solvent. The driving force was provided by applying a back pressure of nitrogen to the feed reservoir for the cell. The results are reported in Table IV, below.

TABLE IV

Selective Removal Of Authentic Solvent
(Acetic Acid) Process Stream Components
Utilizing the Reverse Osmosis Device

| Solvent Process Stream Components Supplied to Reverse Osmosis Device | Weight-% of Component Removed by | |
|---|---|---|
| | DuPont B-15 Membrane | Osmonics MR-01 Membrane |
| Sodium | 46 | 22 |
| Cobalt | 7 | 4 |
| Manganese | 7 | 3 |
| Bromine | 22 | 18 |
| Benzoic Acid | 37 | 27 |
| Phthalic Acid | 15 | 21 |
| Trimellitic Acid | 9 | 8 |
| Membrane Flux (ml/hr-in$^2$) | 0.4 | 0.7 |
| Pressure (psig) | 350 | 350 |
| Temperature (degree F.) | 72 | 72 |

The foregoing results demonstrate that a selective separation of sodium and benzonic acid can be readily achieved by reverse osmosis.

SEPA 50, SEPA 89 and SEPA 92 membranes are all cellulose acetate membranes, commercially available from Osmonics, Inc. of Minnetonka, Minn. The SEPA 50 membrane was utilized at a back pressure of 220 psig; the SEPA 89 and 92 membranes were utilized at a back pressure of 400 psig.

Reverse osmosis membranes suitable for the present purposes are those that are durable under processing conditions (e.g., resistant to acid hydrolysis, swelling, and halides), maintain substantially uniform permablility over extended periods of time, pass through sodium ions and polar aromatic acids such as benzoic acid and the like, but retain relatively larger ions such as cobalt and manganese. The feed flux rate through the membrane preferably is at least about 0.3 gallons/ft$^2$/day and more preferably at least about 5 gallons/ft$^2$/day. These membranes can be incorporated into tubular, spiral-wound, hollow fiber, and the like reverse osmosis devices. Reverse osmosis devices are available as custom or off-the-shelf units from membrane manufacturers such as Osmonics, Inc. and Filmtec Corp.

A variety of membrane materials is commercially available, such as cellulose acetate membranes for example SEPA membranes from Osmonics, Inc., polyamide membranes for example MR-01 from Osmonics, Inc., aramid membranes for example B-15 from DuPont, polysulfone membranes from Millipore, composite thin film membranes from Filmtec Corp., and the like.

What has been illustrated and described herein is a method for selectively removing a number of impurities from a particular process stream. While the present invention has been illustrated and described with reference to a number of embodiments, the present invention is not limited thereto. On the contrary, there are alternatives, changes and modifications will become apparent to those skilled in the art upon reading the foregoing description. Accordingly, such alternatives, changes and modifications are to be considered as forming a part of the invention insofar as they fall within the spirit and scope of the appended claims.

We claim:

1. A method for the continuous catalytic production of an aromatic carboxylic acid product by liquid-phase, exothermic oxidation of an aromatic alkyl with an oxygen-containing gas and a solvent medium in an oxidation reactor, wherein a slurry product stream is withdrawn from the reactor and separated to produce a product-containing stream and at least one mother liquor stream which contains oxidation reaction catalyst and impurities, which includes a step for removing impurities from the mother liquor stream by passing at least a portion of the mother liquor stream through a reverse osmosis separation device and producing a catalyst-bearing stream having a relatively lesser impurities-to-catalyst weight ratio and a purge stream having a relatively greater impurities-to-catalyst weight ratio.

2. The method of claim 1 further including the step of returning at least a portion of the catalyst bearing stream to the reactor.

3. The method of claim 1 wherein said catalyst-bearing stream has a relatively lesser sodium-to-catalyst weight ratio than said purge stream.

4. A method for the continuous, catalytic production of an aromatic carboxylic acid product by liquid-phase, exothermic oxidation of an aromatic alkyl with an oxygen-containing gas and a solvent medium in an oxidation reactor, wherein a slurry product stream is withdrawn from the reactor means and separated to produce a product-containing stream and at least one mother liquor stream which contains oxidation reaction catalyst and impurities, which includes a step for removing impurities from the mother liquor stream by separating the mother liquor stream into a solvent-rich stream and a solvent-depleted stream which contains the oxidation reaction catalyst and the impurities; and passing at least a portion of the solvent-depleted stream through a reverse osmosis separation device while producing a catalyst-bearing stream having a relatively lesser impurities-to-catalyst weight ratio and a purge stream having a relatively greater impurities-to-catalyst weight ratio.

5. The method of claim 4 further including the step of returning at least a portion of the catalyst-bearing stream to the reactor.

6. The method of claim 4 wherein said impurities include sodium ions which are selectively concentrated in said purge stream.

7. The method of claim 4 wherein said catalyst-bearing stream has a relatively lesser sodium-to-catalyst weight ratio and said purge stream has a relatively greater sodium-to-catalyst weight ratio.

8. The method of claim 4 wherein said catalyst-bearing stream has a relatively lesser polar aromatic acid-to-catalyst weight ratio and said purge stream has a relatively greater polar aromatic acid-to-catalyst weight ratio.

* * * * *

UNITED STATES PATENT OFFICE
CERTIFICATE OF CORRECTION

Patent No. 4,855,491      Dated August 8, 1989

Inventor(s) Chew et al.

It is certified that error appears in the above-identified patent and that said Letters Patent is hereby corrected as shown below:

Patent reads:

| Col. | Line | | |
|---|---|---|---|
| Abstract | 3 | "oxidaion" should read | --oxidation-- |
| 3 | 67 | "60," should read | --60-- |
| 6 | 7 | "osmosis cell" -- should read | --osmosis test cell-- |

Signed and Sealed this

Third Day of July, 1990

Attest:

HARRY F. MANBECK, JR.

Attesting Officer     Commissioner of Patents and Trademarks